United States Patent [19]
Johnson et al.

[11] Patent Number: 6,087,350
[45] Date of Patent: Jul. 11, 2000

[54] USE OF PRETREATMENT CHEMICALS TO ENHANCE EFFICACY OF CYTOTOXIC AGENTS

[75] Inventors: Candace S. Johnson; Donald Trump, both of Pittsburg, Pa.

[73] Assignee: University of Pittsburgh of the Commonwealth System of Higher Education, Pittsburgh, Pa.

[21] Appl. No.: 08/921,170

[22] Filed: Aug. 29, 1997

[51] Int. Cl.$^7$ .................................................. A61K 31/59
[52] U.S. Cl. ........................ 514/168; 514/170; 514/653; 514/167; 514/449; 514/110; 514/23
[58] Field of Search .................................. 514/168, 170, 514/167; 552/653

[56] References Cited

U.S. PATENT DOCUMENTS

| | | | |
|---|---|---|---|
| 4,973,721 | 11/1990 | Ikekawa et al. | 552/653 |
| 5,763,429 | 6/1998 | Bishop et al. | 514/168 |
| 5,795,882 | 8/1998 | Bishop et al. | 514/170 |

FOREIGN PATENT DOCUMENTS

| | | | |
|---|---|---|---|
| 93/00079 | 6/1992 | WIPO | A61K 31/10 |
| WO 93/00079 | 1/1993 | WIPO . | |

OTHER PUBLICATIONS

Cho et al., Combined Effects of . . . , Cancer Research, vol. 51. p. 2848–2853, 1991.
Nishio et al., Calcitriol increases . . . , The Cancer Journal, vol. 6, p. 97–101, 1993.
Revillion et al., 1,25–dihydroxyvitamin D3 and . . . , Int.J.Oncol. vol. 5(5), p. 1131–6, 1994.
Abe et al., A novel vitamin . . . , Endocrinology, vol. 129(2), p. 832–837, 1991.
Calverley et al., Vitamin D, Antitumor Steroids, p. 193–270, 1992.
Abe, J. et al., Cancer Res., 46, 6313–6321 (1986).
Abe–Hashimoto, J. et al., Cancer Res., 53, 2534–2537 (1993).
Bilezikian, J.P., The New England Journal of Medicine, 326(18), 1196–1203.
Binderup, E. et al., in Vitamin D: Processings of the 8th Workshop on Vitamin D, Paris, France (A. Norman et al., Eds., Walter de Gruyter, Berlin, 1991, p. 192).
Binderup, L. et al., Biochemical Pharmacology, 42(8), 1569–1575 (1991).
Calverley et al., in Antitumor Steroids (Blickenstaff, R.T., Ed., Academic Press, Orlando, 1992, pp. 193–270).
Campbell, M.J. et al., J. Mol. Endocrinol., 19, 15–27 (1997).
Campbell, M.J. et al., Journal of the National Cancer Institute, 89(3), 182–185 (1997).
Cho, Y.L. et al., Cancer Res., 51, 2848–2853 (1991).
Clark, J.W. et al., J. Cancer Res. Clin. Oncol., 118, 190–194 (1992).
Colston, K. et al., Endocrinology, 108(3), 1083–1086 (1981).
Cross, H.S. et al., Arch. Pharmacol., 347, 105–110 (1993).
DeLuca, H., FASEB J., 2, 224–236 (1988).
Dilworth, F.J. et al., Biochemical Pharmacology, 47(6), 987–993 (1994).

Eisman, J. et al., Cancer Res., 47, 21–25 (1987).
Eisman, J.A. et al., Lancet, 2, 1335–1336 (1979).
Elstner, E. et al., Cancer Research, Aug. 1, 1996, pp. 3570–3576.
Frampton, R.J. et al., Cancer Res., 43, 4443–4447 (1983).
Hengst, L. et al., Science, 271, 1861–1864.
Honma, Y. et al., Proc. Natl. Acad. Sci. USA, 80, 201–204 (1983).
Koeffler, H.P. et al., Cancer Treatment Rep., 69, 1399–1407 (1985).
Liu, M. et al., Genes and Devel., 10, 142–153 (1996).
McCollum, E. et al., J. Biol. Chem., 53, 293–312 (1922).
McElwain, M.C. et al., Mol. Cell. Differ., 3, 31–50 (1995).
Mellanby, E. et al., Lancet, 1, 407–412 (1919).
Miller, G.J. et al., Cancer Res., 52, 515–520 (1992).
Minghetti, P.P. et al., FASEB J., 2, 3043–3053 (1988).
Munker, R. et al., Blood, 88(6), 2201–2209.
Munker, R. et al., J. Clin. Invest., 78, 424–430 (1986).
Peleg, S. et al., Journal of Biological Chemistry, 270 (18), 10551–10558 (1995).
Raina, V. et al., Br. J. Cancer, 63, 4673 (1991).
Rigby, W.F. et al., J. Immunol., 135(4), 2279–2286 (1985).
Russell, R.M., JAMA, 273(21), 1699–1700 (1995).
Saunders, D.E. et al., Gynecologic Oncology, 51, 155–159 (1993).
Saunders, D.E. et al., Abstract 1787, Proc. Am. Cancer Res., 34, 300 (1993).
Smith, J.M. et al., Abstract 761, Proc. Am. Assn. Cancer Res., 34, 128 (1993).
Studzinski, G.P. et al., Critical Reviews in Eukaryotic Gene Expression, 3(4), 279–312 (1993).
Tanaka, H. et al., Clinical Orthopaedics and Related Research, 247, 290–296 (1989).
Tsuchiya, H. et al., Journal of Orthopaedic Research, 11(1), 122–130 (1993).
van den Bemd, G.C.M. et al., Proc. Natl. Acad. Sci. USA, 93, 10685–10690 (1996).
Walters, M.R. Endocr. Rev., 13, 719–764 (1992).
Wang, Q.M. et al., Cancer Res., 56, 264–267 (1996).
Waxman, S. et al., Cancer Res., 50, 3878–3887 (1990).
Xu, H. et al., Experimental Cell Research, 209, 367–374 (1993).
Yu, W. et al., Abstract 1771, Proc. Am. Assn. Cancer Res., 36, 298 (1995).
Zhou, J.Y. et al., Blood, 73, 75–82 (1991).
Saunders, D.E. et al., Abstract No. 2641, Proc. Am. Assoc. for Cancer Research, 33, 442 (1992).
Saunders, D.E. et al., Abstract No. 1949, Proc. Am. Assoc. for Cancer Research, 35, 327 (1994).
Abe et al., Endocrinology, 129 (2), 832–837 (1991).
Jimenez et al., Cancer Res., 52 (18), 5123–5125 (1992).
Nishio et al., Cancer Journal, 6 (2), 97–101 (1993).

Primary Examiner—Marianne M. Cintins
Assistant Examiner—Vickie Kim
Attorney, Agent, or Firm—Leydig, Voit & Mayer, Ltd.

[57] ABSTRACT

The present invention provides a method of killing a cell by first administering to the cell a vitamin D derivative and subsequently administering to the cell a cytotoxic agent. Where the cell is within a tumor, the present invention provides a method of retarding the growth of the tumor by first administering the vitamin D derivative to the tumor and subsequently administering to the tumor the cytotoxic agent.

34 Claims, 10 Drawing Sheets

LEGEND
O = CDDP alone
▲ = Concurrent CDDP and Ro23-7553 (4μM)
△ = Pretreatment with 2μM Ro23-7553 then cDDP
● = Pretreatment with 4μM Ro23-7553 then cDDP LEGEND
○ = Ro23-7553 alone
● = Pretreatment with Ro23-7553 then cDDP
▼ = cDDP alone LEGEND
○ = Carboplatin alone
● = Pretreatment with 1,25 $D_3$, then carboplatin LEGEND
O = 1,25 D₃ alone
● = Pretreatment with 1,25 D₃, then carboplatin LEGEND
O = Paclitaxel alone
▲ = 1,25 $D_3$ alone
● = Pretreatment with 1,25 $D_3$, then paclitaxel

USE OF PRETREATMENT CHEMICALS TO ENHANCE EFFICACY OF CYTOTOXIC AGENTS

STATEMENT AS TO RIGHTS TO INVENTIONS MADE UNDER FEDERALLY SPONSORED RESEARCH AND DEVELOPMENT

This invention was made with Government support under Grant Number RO1-CA67267 awarded by the National Cancer Institute of the National Institutes of Health. The United States Government may have certain rights in this invention.

TECHNICAL FIELD OF THE INVENTION

The present invention relates to the use of vitamin D derivatives to enhance efficacy of cytotoxic agents.

BACKGROUND OF THE INVENTION

Combating the growth of neoplastic cells and tumors has been a major focus of biological and medical research. Such research has led to the discovery of novel cytotoxic agents potentially useful in the treatment of neoplastic disease. Examples of cytotoxic agents commonly employed in chemotherapy include anti-metabolic agents interfering with microtubule formation, alkylating agents, platinum-based agents, anthracyclines, antibiotic agents, topoisomerase inhibitors, and other agents.

Aside from merely identifying potential chemotherapeutic agents, cancer research has led to an increased understanding of the mechanisms by which these agents act upon neoplastic cells, as well as on other cells. For example, cholecalciferol (vitamin D) can effect differentiation and reduce proliferation of several cell types cells both in vitro and in vivo. The active metabolite of vitamin D (1,25-dihydroxycholecalciferol (hereinafter "1,25$D_3$") and analogs (e.g., 1,25-dihydroxy-16-ene-23-yne-cholecalciferol (Ro23-7553), 1,25-dihydroxy-16-ene-23-yne-26,27-hexafluoro-19-nor-cholecalciferol (Ro25-6760), etc.) mediate significant in vitro and in vivo anti-tumor activity by retarding the growth of established tumors and preventing tumor induction (Colston et al., *Lancet*, 1, 188 (1989); Belleli et al., *Carcinogenesis*, 13, 2293 (1992); McElwain et al., *Mol. Cell. Diff.*, 3, 31–50 (1995); Clark et al., *J. Cancer Res. Clin. Oncol.*, 118, 190 (1992); Zhou et al., *Blood*, 74, 82–93 (1989)). In addition to retarding neoplastic growth, 1,25$D_3$ induces a $G_0/G_1$-S phase block in the cell cycle (Godyn et al, *Cell Proliferation*, 27, 37–46 (1994); Rigby et al., *J. Immunol.*, 135, 2279–86 (1985); Elstner et al., *Cancer Res.*, 55, 2822–30 (1995); Wang et al., *Cancer Res.*, 56, 264–67 (1996)). These properties have led to the successful use of 1,25$D_3$ to treat neoplastic tumors (see Cunningham et al., *Br. J. Cancer*, 63, 4673 (1991); Mackie et al., *Lancet*, 342, 172 (1993), Bower et al., *Proc. Am. Assoc. Cancer. Res.*, 32, 1257 (1991)).

In addition to its antineoplastic and cell-cycle blocking effects, 1,25$D_3$ treatment can lead to hypercalcemia. As a result, 1,25$D_3$ is typically administered for therapeutic applications (e.g., metabolic bone disease) at relatively low doses (e.g., about 1 μg/day to about 2 μg/day) long term. To mitigate the effects of hypercalcemia, analogs have been developed which retain antiproliferative activity without inducing hypercalcemia. (See, e.g., Zhou et al., *Blood*, 73, 75 (1991); Binderup et al., *Biochem. Pharmacol.*, 42, 1569 (1991); Binderup et al., page 192 in *Proceedings of the 8th Workshop on Vitamin D*, Paris France (Norman, A. et al., Eds., Walter de Gruyter, Berlin, (1991))). Many of these synthetic analogs are more potent than 1,25$D_3$ in inhibiting neoplastic growth (for a review of many such analogs, see Calverley et al., "Vitamin D" in *Antitumor Steroids* (Blickenstaff, R. T., Ed., Academic Press, Orlando (1992))).

The platinum-based agents are widely utilized in chemotherapeutic applications. For example, cisplatin kills tumor cells via formation of covalent, cross- or intrastrand DNA adducts (Sherman et al. *Chem. Rev.*, 87, 1153–81 (1987); Chu, *J. Biol. Chem.*, 269, 787–90 (1994)). Treatment with such platinum-based agents thereby leads to the inhibition of DNA synthesis (Howle et al., *Biochem. Pharmacol.*, 19, 2757–62 (1970); Salles et al., *Biochem. Biophys. Res. Commun.*, 112, 555–63 (1983)). Thus, cells actively synthesizing DNA are highly sensitive to cisplatin (Roberts et al., *Prog. Nucl. Acid Res. Mol. Biol.*, 22, 71–133 (1979); Pinto et al., *Proc. Nat. Acad. Sci.* (Wash.) 82, 4616–19 (1985)). Such cells generally experience a growth arrest in $G_2$ and eventually undergo apoptosis. This apoptotic effect is observed at drug concentrations insufficient to inhibit DNA synthesis (Sorenson et al., *J. Natl. Cancer Inst.*, 82, 749–55 (1990)), suggesting that platinum agents act on neoplastic cells via multiple mechanisms. Some cells also demonstrate increased platinum sensitivity when in the $G_1$ phase of the cell cycle (Krishnaswamy et al., *Mutation Res.*, 293, 161–72 (1993); Donaldson et al., *Int. J. Cancer*, 57, 847–55 (1994)). Upon release from $G_0/G_1$-S block, such cells remain maximally sensitized through the remainder of the cell cycle.

Other chemotherapeutic agents act by different mechanisms. For example, agents interfering with microtubule formation (e.g., vincristine, vinblastine, paclitaxel, docetaxel, etc.) act against neoplastic cells by interfering with proper formation of the mitotic spindle apparatus (see, e.g., Manfredi et al., *Pharmacol. Ther.*, 25, 83–125 (1984)). Thus, agents interfering with microtubule formation mainly act during the mitotic phase of the cell cycle (Schiff et al., *Proc. Nat. Acad. Sci. U.S.A.*, 77, 1561–65 (1980); Fuchs et al., *Cancer Treat. Rep.*, 62, 1219–22, (1978); Lopes et al., *Cancer Chemother. Pharmacol.*, 32, 235–42 (1993)). Antimetabolites act on various enzymatic pathways in growing cells. For example, methotrexate (MTX) is a folic acid analog which inhibits dihydrofolate reductase. As a result, it blocks the synthesis of thymidylate and purines required for DNA synthesis. Thus, the primary impact of MTX is in the S phase of the cell cycle, but it can also impact RNA synthesis in $G_1$ and $G_2$ (Olsen, *J. Am. Acad. Dermatol.*, 25, 306–18 (1991)).

Because of the differences in the biological mechanisms of various cytotoxic agents, protocols involving combinations of different cytotoxic agents have been attempted (e.g., Jekunen et al., *Br. J. Cancer*, 69, 299–306 (1994); Yeh et al., *Life Sciences*, 54, 431–35 (1994)). Combination treatment protocols aim to increase the efficacy of cytopathic protocols by using compatible cytotoxic agents. In turn, the possibility that sufficient antineoplastic activity can be achieved from a given combination of cytotoxic agents presents the possibility of reducing the dosage of individual cytotoxic agents to minimize harmful side effects. In part because the various cytotoxic agents act during different phases of the cell cycle, the success of combination protocols frequently depends upon the order of drug application (e.g., Jekunen et al., supra; Studzinski et al., *Cancer Res.*, 51, 3451 (1991).

There have been attempts to develop combination drug protocols based, in part, on vitamin D derivatives. For example, the inhibitory effect of concurrent combination of 1,25$D_3$ and platinum drugs on the growth of neoplastic cells has been studied (Saunders et al., *Gynecol. Oncol.*, 51, 155–59 (1993); Cho et al., *Cancer Res.*, 51, 2848–53 (1991)), and similar studies have focused on concurrent combinations of $1,25D_3$ and other cytotoxic agents (Tanaka et al., *Clin. Orthopaed. Rel. Res.*, 247, 290–96 (1989)). The results of these studies, however, have been less than satisfactory. In particular, the optimal sequence of drug administration has not been achieved. Moreover, the application of these approaches in therapy would require the long-term application of high doses of $1,25D_3$ in some protocols, which, as mentioned, can precipitate significant side effects. Thus, there remains a need for an improved method of enhancing the efficacy of chemotherapeutic agents, particularly a need for an improved combination therapy, especially involving vitamin D derivatives.

BRIEF SUMMARY OF THE INVENTION

The present invention provides a method of killing a cell by first administering to the cell a vitamin D derivative and subsequently administering to the cell a cytotoxic agent. Where this strategy is applied to an intact tumor, the present invention provides a method of retarding the growth of the tumor by first administering the vitamin D derivative to the tumor and subsequently administering the cytotoxic agent.

In some applications, the present inventive method is a useful therapy, particularly in the treatment of neoplastic or cancerous diseases. In other applications, the present invention provides a tool for further research pertaining to subjects including neoplastic cell growth, the control and regulation of the cell cycle, and the mechanism and efficacy of cytotoxicity and chemotherapy. In this respect, the inventive method is useful for the development of more refined therapies. The invention can best be understood with reference to the accompanying drawings and in the following detailed description of the preferred embodiments.

BRIEF DESCRIPTION OF THE DRAWINGS

FIG. 6a depicts the results from varying dosage of carboplatin. FIG. 6b depicts the results from varying dosage of $1,25D_3$. Each point is the mean±SD total clonogenic cells/gm tumor (3–5-group). Values significantly different from $1,25D_3$ or carboplatin alone are shown with an asterisk: $*p<0.001$ (ANOVA).

DESCRIPTION OF THE PREFERRED EMBODIMENTS

Figure 1:
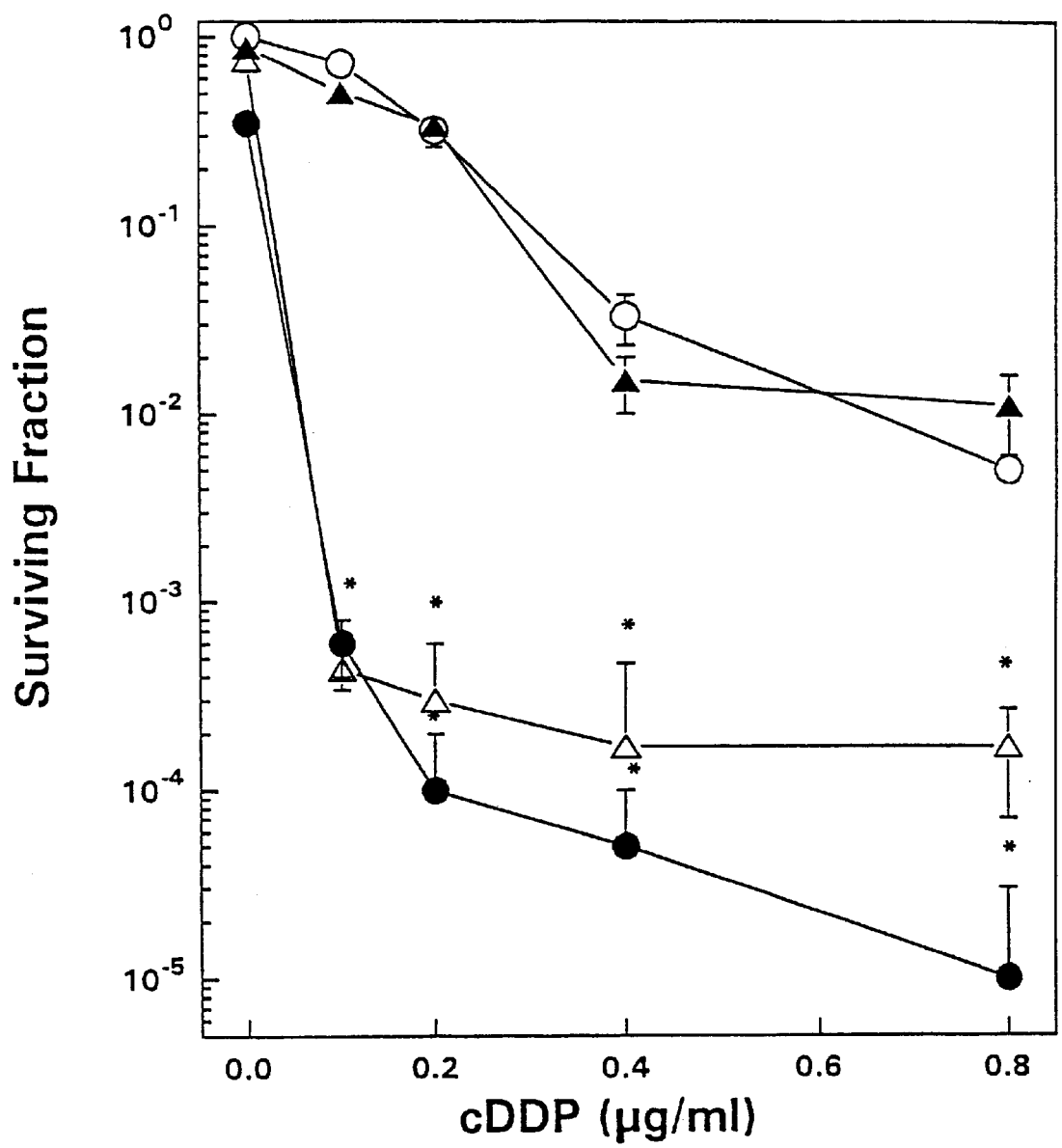
FIG. 1 graphically represents the effect of Ro23-7553 on in vitro cisplatin-mediated cytotoxicity. Each point represents the mean±SD for the surviving fraction of 3 replicates from a representative experiment that was replicated 2–3 times. Values significantly different than cisplatin alone or concurrent cisplatin and Ro23-7553 are shown with an asterisk: $*p<0.001$ (ANOVA).

As used herein, including the claims appended hereto, the term "cytotoxic agent" refers to any compound mediating cell death by any mechanism including, but not limited to, inhibition of metabolism or DNA synthesis, interference with cytoskeletal organization, destabilization or chemical modification of DNA, apoptosis, etc. A compound is an "analog" of a biologically active compound if the analog elicits some, but not necessarily all, of the physiological responses of the biologically active compound when administered in vivo. "Neoplastic" denotes a type of cell exhibiting uncontrolled proliferation; generally, mitotic progeny of a neoplastic cell are also neoplastic in character and do not terminally differentiate in vivo in response to physiologically normal (i.e., nonpathological) endogenous (i.e., not exogenous or invasive) environmental cues. Neoplastic cells include cancerous and transformed cells. Neoplastic cells can be isolated (e.g., a single cell in culture or a metastatic or disseminated neoplastic cell in vivo) or present in an agglomeration, either homogeneously or in heterogeneous combination with other cell types (neoplastic or otherwise) in a tumor or other collection of cells. In this regard, a tumor includes any collection of cells (neoplastic or otherwise) in which at least some of the member cells are physically associated with at least some other member cells through a common extracellular matrix. Thus, a tumor includes tissue grown in vivo and also associations of cells formed in vitro, such as colonies.

The present invention provides a method of killing a cell by first administering to the cell a vitamin D derivative and subsequently administering a cytotoxic agent to the cell. Preferably, the cell is a neoplastic cell as defined herein. The cell can be solitary and isolated from other like cells (such as a single cell in culture or a metastatic or disseminated neoplastic cell in vivo), or the cell can be a member of a collection of cells (e.g., within a tumor).

Where the cell is within a tumor, the present invention provides a method of retarding the growth of the tumor by first administering the vitamin D derivative to the tumor and subsequently administering the cytotoxic agent to the tumor. By virtue of the cytopathic effect on individual cells, the present inventive method reduces or substantially eliminates the number of cells added to the tumor mass over time. Preferably, the inventive method effects a reduction in the number of cells within a tumor, and, most preferably, the method leads to the partial or complete destruction of the tumor (e.g., via killing a portion or substantially all of the cells within the tumor).

Where the cell is associated with a neoplastic disorder within a mammal (e.g., a human), the invention provides a method of treating the mammal by first administering the vitamin D derivative to the mammal and subsequently administering the cytotoxic agent to the mammal. This approach is effective in treating mammals bearing intact or disseminated cancer. For example, where the cells are disseminated cells (e.g., metastatic neoplasia), the cytopathic effects of the inventive method can reduce or substantially eliminate the potential for further spread of neoplastic cells throughout the mammal, thereby also reducing or minimizing the probability that such cells will proliferate to form novel tumors within the mammal. Furthermore, by retarding the growth of tumors including neoplastic cells, the inventive method reduces the likelihood that cells from such tumors will eventually metastasize or disseminate. Of course, when the present inventive method achieves actual reduction in tumor size (and especially elimination of the tumor), the inventive method attenuates the pathogenic effects of such tumors within the mammal. Another application is in high-dose chemotherapy requiring bone marrow transplant or reconstruction (e.g., to treat leukemic disorders) to reduce the likelihood that neoplastic cells will persist or successfully regrow.

Without being bound by any particular theory, it is believed that the inventive method effects cytotoxicity of neoplastic cells by inducing a $G_0/G_1$-S phase block in the cell cycle, as mentioned herein. The cells are sensitized to cytotoxic agents able to act on cells in such a blocked stage. Alternatively, synchronization of the release of the cells from the block can render them collectively sensitive to the effects of agents acting later in the cell cycle. Thus, for employment in the inventive method, any vitamin D derivative suitable for potentiating the cytotoxic effect of chemotherapeutic agents upon pretreatment can by utilized. For example, the vitamin D derivative can be vitamin D or its natural metabolite ($1,25D_3$). However, as discussed herein, many vitamin D analogs have greater antitumor activity than the native metabolite; thus the vitamin D derivative can be such an analog of $1,25D_3$. Furthermore, where the inventive method is used for therapeutic applications, the vitamin D derivative can be a nonhypercalcemic analog of $1,25D_3$, as such analogs reduce or substantially eliminate the hypercalcemic side effects of vitamin D-based therapy. For example, the analog can be Ro23-7553 or Ro24-5531, or another analog.

The vitamin D derivative can be provided to the cells or tumors in any suitable manner, which will, of course, depend upon the desired application for the inventive method. Thus, for example, for in vitro applications, the vitamin D derivative can be added to the culture medium (e.g., mixed initially with the medium or added over time). For in vivo applications, the vitamin D derivative can be mixed into an appropriate vehicle for delivery to the cell or tumor. Thus, for systemic delivery, the vitamin D derivative can be supplied by subcutaneous injection, intravenously, orally, or by other suitable means. Of course, the vitamin D derivative can be provided topically (e.g., by application of a salve or cream comprising the vitamin D derivative to a tumor, by injection of a solution comprising the vitamin D derivative into a tumor, etc.).

As mentioned, the present inventive method involves pretreating the cells or tumors with the vitamin D derivative. Any period of pretreatment can be employed in the present inventive method; the exact period for vitamin D derivative pretreatment will vary depending upon the application for the inventive method. For example, in therapeutic applications, such pretreatment can be for as little as about a day to as long as about 5 days; more preferably, the pretreatment period is between about 2 and 4 days (e.g., about 3 days).

The dose of vitamin D derivative provided to the cells can vary depending upon the desired application. In research, for example, the dose can vary considerably, as dose-response analysis might be a parameter in a given study. For therapeutic applications, because the pretreatment period is so brief in comparison with standard vitamin D-based therapies, higher than typical doses (as discussed above) of the vitamin D derivative can be employed in the present inventive method without a substantial risk of hypercalcemia. Thus, for example, in a human patient, as little as 1 $\mu$g/day of vitamin D derivative (which as mentioned above, is within the normal dosage for $1,25D_3$) can be supplied to a human patient undergoing treatment, while the maximal amount can be as high as about 20 $\mu$g/day (or even higher in some larger patients). Preferably, however, between about 4 $\mu$g/day and about 15 $\mu$g/day (e.g., between about 7 $\mu$g/day and about 12 $\mu$g/day) of the vitamin D derivative is delivered to the patient. Typically, the amount of vitamin D derivative supplied will not be so great as to pose a significant risk of inducing hypercalcemia or provoking other toxic side effects. Hence, where non-hypercalcemic vitamin D derivatives are used, higher amounts still can be employed. Thus, 30 $\mu$g/day or more (e.g., about 40 $\mu$g/day or even 50 $\mu$g/day or more) non-hypercalcemic vitamin D derivative can be delivered to a human patient during pretreatment in accordance with the present inventive method. Of course, the exact dose of vitamin D derivative will depend upon the size of the patient and the mode and timing of delivery. The determination of such doses is well within the ordinary skill in the art.

Following pretreatment with the vitamin D derivative, the inventive method involves administering a cytotoxic agent. Following pretreatment, the cytotoxic agent can be administered either alone or in combination with continued administration of the vitamin D derivative following pretreatment. Any cytotoxic agent can be employed in the present inventive method; as mentioned, many cytotoxic agents suitable for chemotherapy are known in the art. For example, the cytotoxic agent can be an antimetabolite (e.g., 5-flourouricil (5-FU), methotrexate (MTX), fludarabine, etc.), an anti-microtubule agent (e.g., vincristine, vinblastine, taxanes (such as paclitaxel and docetaxel), etc.), an alkylating agent (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, camptothecins), or other cytotoxic agents. The choice of cytotoxic agent depends upon the application of the inventive method. For research, any potential cytotoxic agent (even a novel cytotoxic agent) can be employed to study the effect of the toxin on cells or tumors pretreated with vitamin D derivatives. For therapeutic applications, the selection of a suitable cytotoxic agent will often depend upon parameters unique to a patient; however, selecting a regimen of cytotoxins for a given chemotherapeutic protocol is within the skill of the art.

In many instances, the pretreatment of cells or tumors with the vitamin D derivative before treatment with the cytotoxic agent effects an additive and (as demonstrated in the following examples) often synergistic degree of cell death. Such synergy is often achieved with cytotoxic agents able to act against cells in the $G_0$-$G_1$ phase of the cell cycle, and such cytotoxic agents are preferred for use in the present inventive methods. Examples of such preferred cytotoxic agents are platinum-based agents, paclitaxel, and cyclophosphamide.

EXAMPLES

The following none examples demonstrate the efficacy of the present invention. In particular, the examples demonstrate that pretreatment of neoplastic cells with $1,25D_3$ or its non-hypercalcemic analogs enhances the efficacy of several traditional cytotoxic agents and that such potentiation is more effective than concurrent administration. These examples are included here merely for illustrative purposes and should not be construed so as to limit any aspect of the claimed invention.

Example 1

This example explains the materials and general methods employed in the following examples.

Inbred female C3H/HeJ mice age 6–10 weeks were obtained from Jackson Laboratories. The mice were virus antibody free, age and weight matched for experimental use and were fed a balanced rodent diet.

SCCVII/SF cells, a murine, rapidly growing, non-metastasizing squamous tumor line, were maintained in vivo in C3H/HeJ mice as described previously (McElwain et al., *Mol. Cell. Diff.*, 3, 31–50 (1995)) by s.c. inoculation of $5\times10^5$ log-phase tissue culture cells in the right flank of the animal. The SCCVII/SF cell line was maintained in vitro in RPMI-1640 supplemented with 12.5% inactivated fetal bovine serum (FCS) and 1% penicillin-streptomycin sulfate.

$1,25D_3$ and its non-hypercalcemic analog, Ro23-7553, were initially stored in pure powder form in a sealed light-protective vessel at 4° C. For use, each drug was reconstituted in 100% ethyl alcohol and maintained as described (McElwain et al., *Mol. Cell. Diff.*, 3, 31–50 (1995)). The cytotoxic agents (carboplatin, cisplatin (i.e., cDDP), and paclitaxel) were diluted in 0.9% saline and were injected i.p. at various doses in a total volume of 0.2 ml, during the experimental protocols.

The in vitro cytotoxicity of drug on tumor cells was determined via the in vitro clonogenic assay (McElwain et al., *Mol. Cell. Diff.*, 3, 31–50 (1995)) with minor modifications as described herein. Briefly, murine SCCVII/SF cells were pre-treated with either 2 nM or 4 nM $1,25D_3$ or Ro23-7553. While $1,25D_3$ or Ro23-7553 are not stable for long periods in tissue culture media, anti-proliferative effects are observed at 24 hr, 48 hr and 7 day incubation times (McElwain et al., supra). After 48 hours incubation with $1,25D_3$ or Ro23-7553, cells were treated for 2 hours with varying concentrations of cytotoxic agent, washed with RPMI 1640 plus FCS, and plated in various dilutions in 6-well tissue culture plates. Following a 7 day incubation at 37° C. in 5% $CO_2$, monolayers were washed with saline, fixed with 100% methanol, stained with 10% Giemsa, and colonies were counted under light microscopy. The surviving fraction was calculated by dividing the cloning efficiency of treated cells by the cloning efficiency of untreated controls.

The effect of $1,25D_3$ or Ro23-7553 alone and/or in combination with various cytotoxic agents on tumor cells in vivo was determined by a modification of the in vivo excision clonogenic tumor cell survival assay (Johnson et al., *Cancer Chemother. Pharmacol.*, 32, 339–46 (1993)). Briefly, SCCVII/SF tumor bearing animals at 14 days post implantation were treated i.p. for 3 days with $1,25D_3$ or Ro23-7553 at either 0.5 mg/kg/day or at varying doses of 0.03125–0.5 mg/kg/day. On day 3, animals also received an i.p. dose of either 6 mg/kg or varying doses of 1–6 mg/kg of cytotoxic agent. After 24 hours, aliquots of minced tumor were enzymatically dissociated for 60 min at room temperature with a mixture of type I collagenase (37.5 mg/ml), DNAse (55 mg/ml) and EDTA (1%). Viable tumor cells (determined by trypan blue staining) were then plated at various dilutions. After 7 days incubation, colonies were counted and numbers of clonogenic cells per gram of tumor counted. The mean±standard deviation (SD) cell yield, cloning efficiency, and number of clonogenic cells for control (no treatment) tumors (n=40) averaged $139.4\pm38.2\times10^6$ viable tumor cells/g tumor, $27.0\pm0.56\%$, and $37.5\pm13.3\times10^6$ clonogenic tumor cells/g tumor, respectively. The surviving fraction per gram of tumor is defined as the number of clonogenic tumor cells per gram of treated tumor divided by the number of clonogenic tumor cells per gram of control (untreated) tumor. This assay is an accurate measure of in vivo anti-tumor activity; a surviving fraction less than 0.1 correlates with an actual decrease in tumor volume and an increase in tumor regrowth delay (Braunschweiger et al., *Cancer Res.*, 48, 6011–16 (1988); Braunschweiger et al., *Cancer Res.*, 51, 5454–60 (1991)).

The effect of $1,25D_3$ or Ro23-7553 alone and/or in combination with various cytotoxic agents on tumor cells in vivo was further assayed by measuring the delay of tumor growth (tumor regrowth assay). SCCVII/SF tumor cells ($5\times10^5$) were inoculated s.c. into the flank of the leg of C3H/HeJ mice. On day 9 post implantation, as the tumors were palpable (approximately 5×5 mm), animals were randomized for treatment with low dose i.p. Ro23-7553 (0.214 µg/kg/day) or $1,25D_3$ (0.2 µg/mouse) using a micro-osmotic pump for continuous delivery over seven days. After 7 days, 6 mg/kg cytotoxic agent was injected i.p. Control animals received either treatment alone or no treatment. No treatment animals were given injection of vehicle (PBS) alone or sham pumps were implanted. Tumor growth was assessed by measuring the tumor diameter with calipers three times weekly. Tumor volumes were calculated by the formula: volume=length×(width$^2$)/2. Post-treatment volumes were expressed as a fraction of pre-treatment volume at the time of initial treatment. Tumor regrowth delay was calculated as the mean±standard deviation of the difference in time for treated and control tumor volumes to reach 4 times the pretreatment volume.

Example 2

This example demonstrates the potential for sensitizing tumor cells to the effects of conventional cytotoxic cisplatin therapy by pretreatment with a vitamin D derivative.

Cisplatin (i.e., cDDP) and Ro23-7553 were tested alone and in combination using the in vitro clonogenic assay for the SCCVII/SF tumor cell line as described above. As shown in FIG. 1, pre-treatment of cells with both 2 and 4 nM Ro23-7553 significantly enhanced clonogenic cell kill when compared to cisplatin alone or in concurrent administration (i.e., no pre-treatment) of cisplatin in combination with Ro23-7553. Significant enhancement of cisplatin-mediated cytotoxicity was observed even at low doses of cisplatin.

Example 3

This example demonstrates the enhancement of in vivo cisplatin-mediated anti-tumor activity by pretreatment with a vitamin D derivative.

Figure 2:
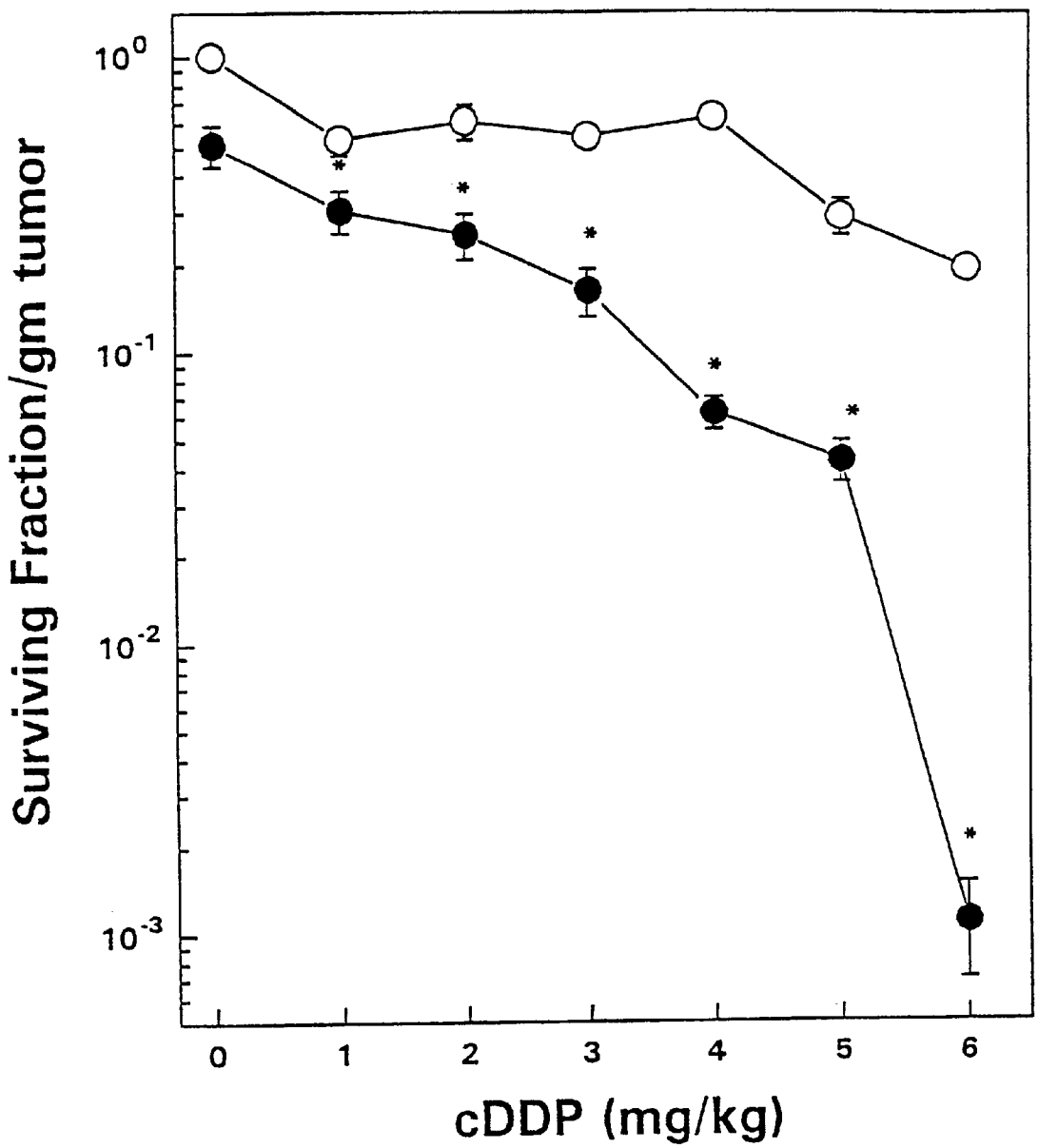
FIG. 2 is a graphic depiction of cisplatin dose-dependent in vivo clonogenic tumor-cell kill following Ro23-7553 pre-treatment. Each point represents the mean±SD surviving fraction for total clonogenic cells/g tumor from a representative experiment that was replicated 2–3 times. Values significantly different than cisplatin alone are shown with an asterisk: $*p<0.001$ (ANOVA).

The excision clonogenic kill assay was employed wherein SCCVII/SF tumor bearing animals at 14 days post implantation were treated i.p. for 3 days with 0.5 mg/kg/day of Ro23-7553. On the third day animals received varying doses of cisplatin. After 24 hours, tumors were harvested, dissociated, and plated for a 7 day incubation. As shown in FIG. 2, pre-treatment for 3 days with the Ro23-7553 before cisplatin resulted in a significant enhancement of clonogenic cell kill when compared to animals treated with cisplatin or Ro23-7553 alone. A significant increase in clonogenic tumor cell kill was observed at each cisplatin dose tested as compared to cisplatin alone.

Figure 3:
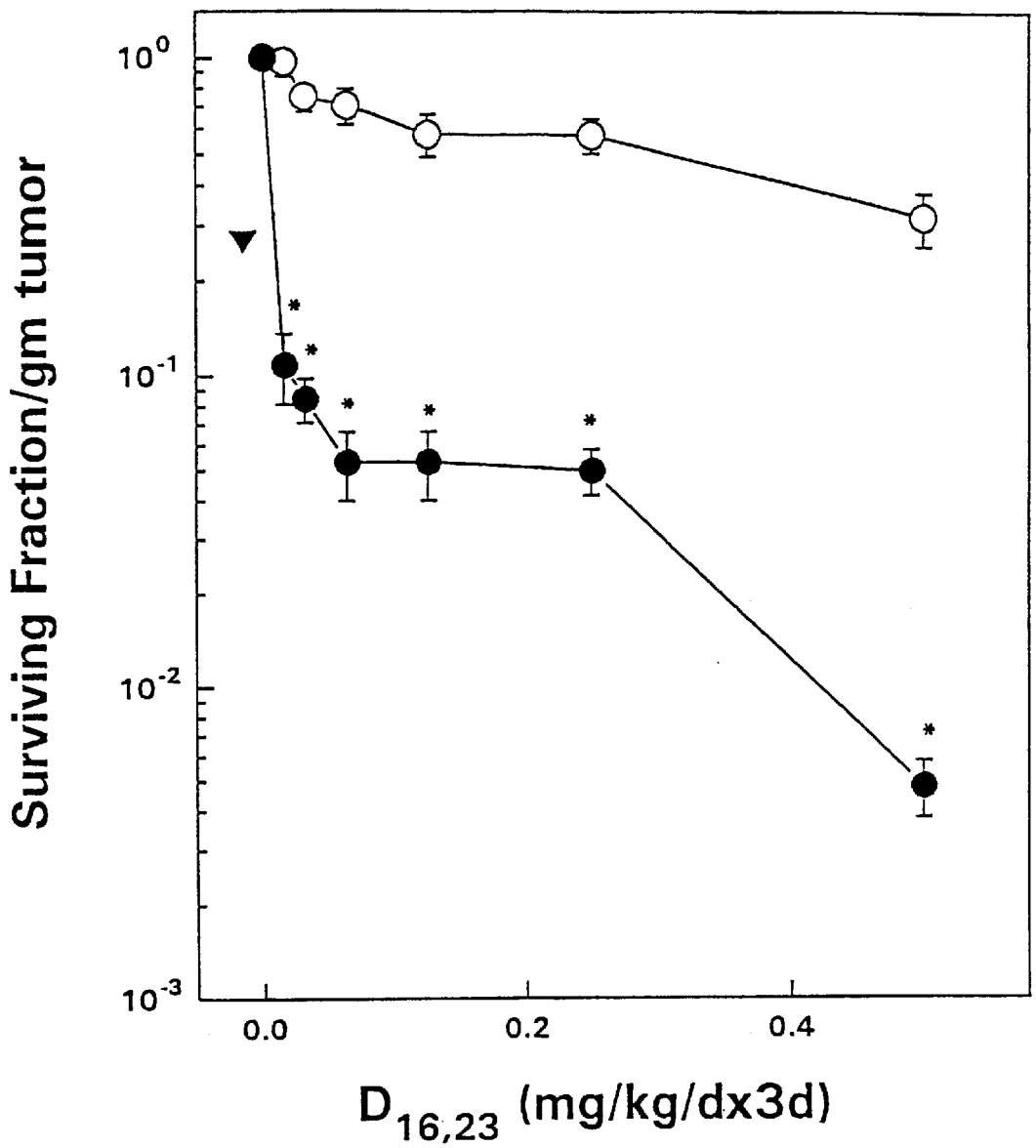
FIG. 3 graphically represents the enhancement of cisplatin-mediated tumor cell kill following pretreatment with low doses of Ro23-7553. Each point represents the mean±SD surviving fraction for total clonogenic cells/g of tumor (3–5 mice/treatment group) from a representative experiment that was replicated 2–3 times. Values significantly different from Ro23-7553 or cisplatin alone are shown with an asterisk: $*p<0.01$ (ANOVA).

To determine the effect of varying the Ro23-7553 dose in this assay, SCC tumor-bearing mice were treated daily for 3 days with from 0.03125 mg/kg/day to 0.5 mg/kg/day Ro23-7553. On day 3, cisplatin was administered at 6 mg/kg. As shown in FIG. 3, Ro23-7553 was capable of significantly enhancing cisplatin-mediated tumor cell kill even at the lowest doses tested as compared to cisplatin or Ro23-7553 alone. No animals in either experimental approaches became hypercalcemic at any of the Ro23-7553 doses.

Example 4

This example demonstrates the enhancement of in vivo cisplatin-mediated anti-tumor activity by pretreatment with a vitamin D derivative.

Figure 4:
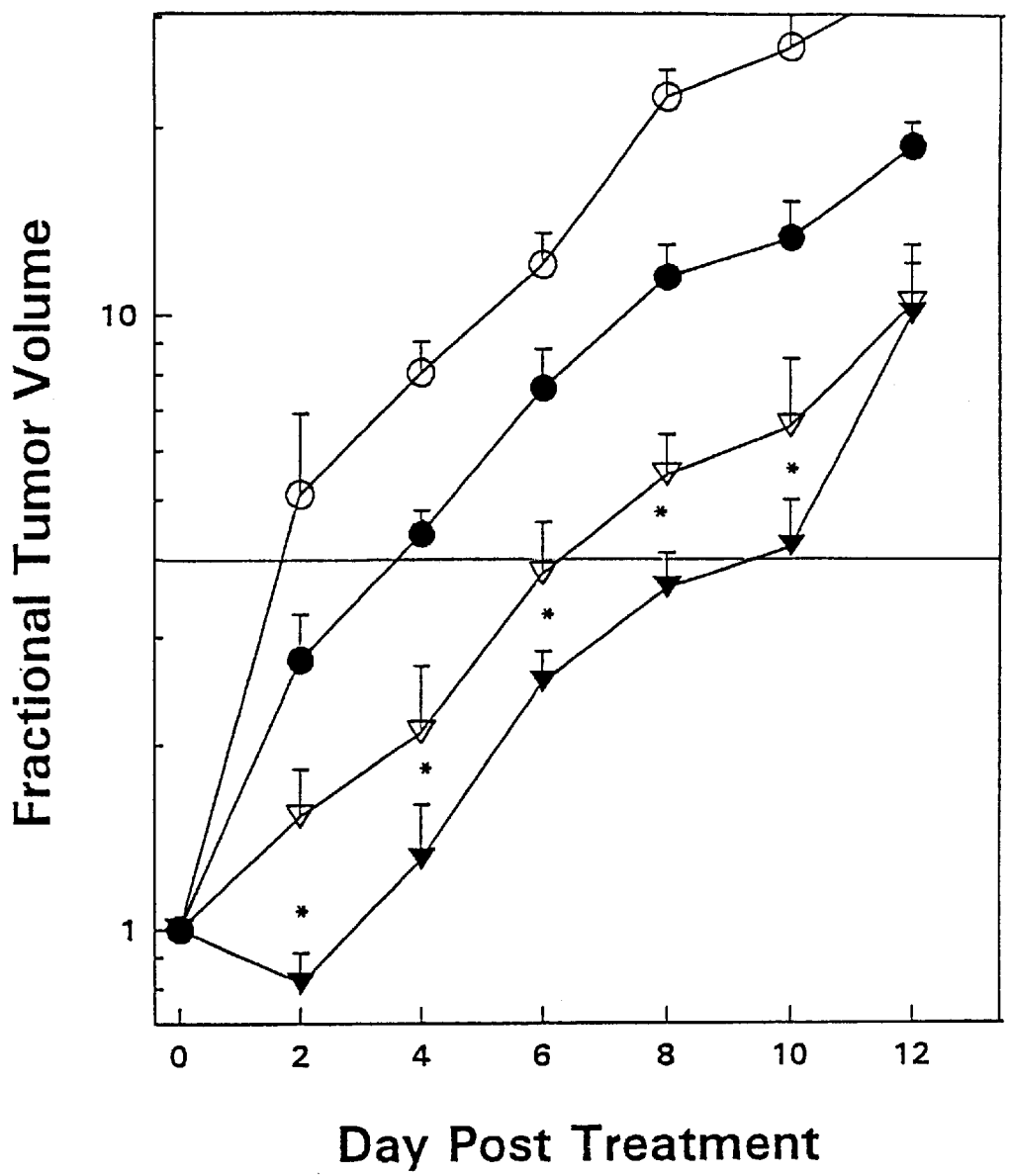
FIG. 4 is a graphic representation of the effect on fractional tumor volume of Ro23-7553 treatment before cisplatin. Each point represents the mean±SD for 8–10 animals from a representative experiment that was replicated 2–3 times. Values significantly different from cisplatin alone are shown with an asterisk: $*p<0.001$ (ANOVA). The dotted line represents 4× pre-treatment control tumor size.

The tumor regrowth assay was employed wherein SCCVII/SF tumor-bearing mice (day 9 post implantation) were treated with Ro23-7553 administered continuously. At the end of Ro23-7553 administration, cisplatin was injected i.p. at 6 mg/kg. No treatment or single treatment animals were injected with vehicle (PBS) or implanted with sham pumps depending on the treatment group. As shown in FIG. 4, animals experienced a significant decrease in fractional tumor volume when pre-treated with Ro23-7553 before cisplatin as compared to treatment with either agent alone. When tumor regrowth delay (mean±SD of the difference in time for treated and control tumors to reach 4× pretreatment size as represented by the dotted line in FIG. 4) was examined, a significant increase was observed in animals treated with Ro23-7553 plus cisplatin as compared either to cisplatin or Ro23-7553 alone. These results are presented in table 1.

TABLE 1

Effect of Ro23-7553 and Cisplatin on Tumor Regrowth Delay

| Treatment | Tumor Regrowth Delay |
| --- | --- |
| Ro23-7553 | 1.8 + 0.8 |
| cisplatin (6 mg/kg) | 4.4 + 0.3 |
| Ro23-7553/cisplatin | 7.7 + 0.4 |

Example 5

This example demonstrates the potential for sensitizing tumor cells to the effects of conventional cytotoxic carboplatin therapy by pretreatment with a vitamin D derivative.

Figure 5:
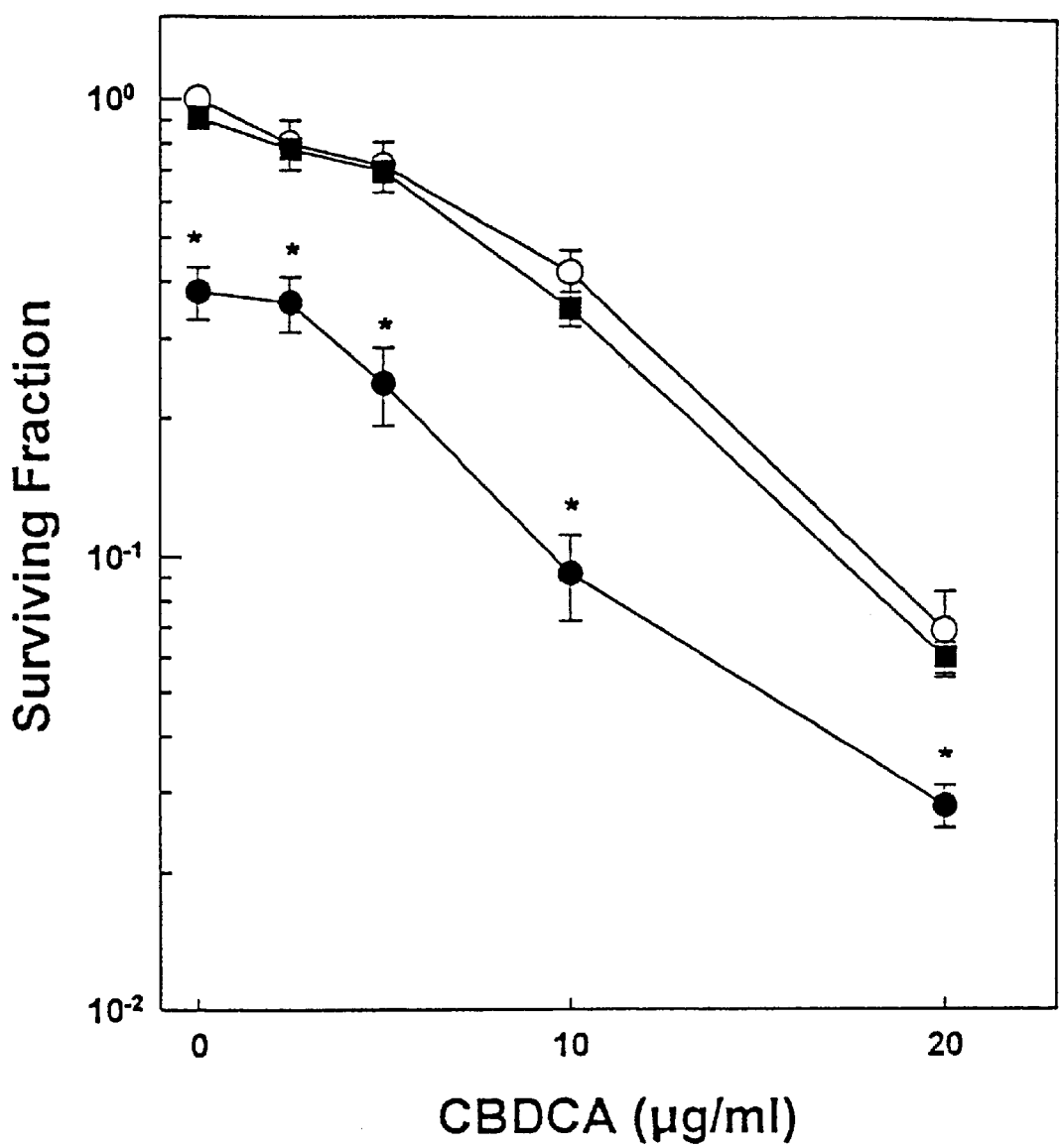
FIG. 5 is a graphic depiction of the effect of carboplatin-mediated cytotoxicity after pre-treatment of cells with $1,25D_3$. Each point is the mean±SD (3 replicates). Values significantly different than carboplatin alone are shown with an asterisk: $*p<0.001$ (ANOVA).

Carboplatin (i.e., CBDCA) and $1,25D_3$ were tested alone and in combination using the in vitro clonogenic assay as described above. As shown in FIG. 5, pre-treatment of cells with 2 nM $1,25D_3$ for 48 hours significantly enhanced clonogenic cell kill when compared to carboplatin alone or in concurrent administration (i.e., no pre-treatment) of carboplatin in combination with $1,25D_3$.

Example 6

This example demonstrates the enhancement of in vivo carboplatin-mediated anti-tumor activity by pretreatment with a vitamin D derivative.

Figure 6A:
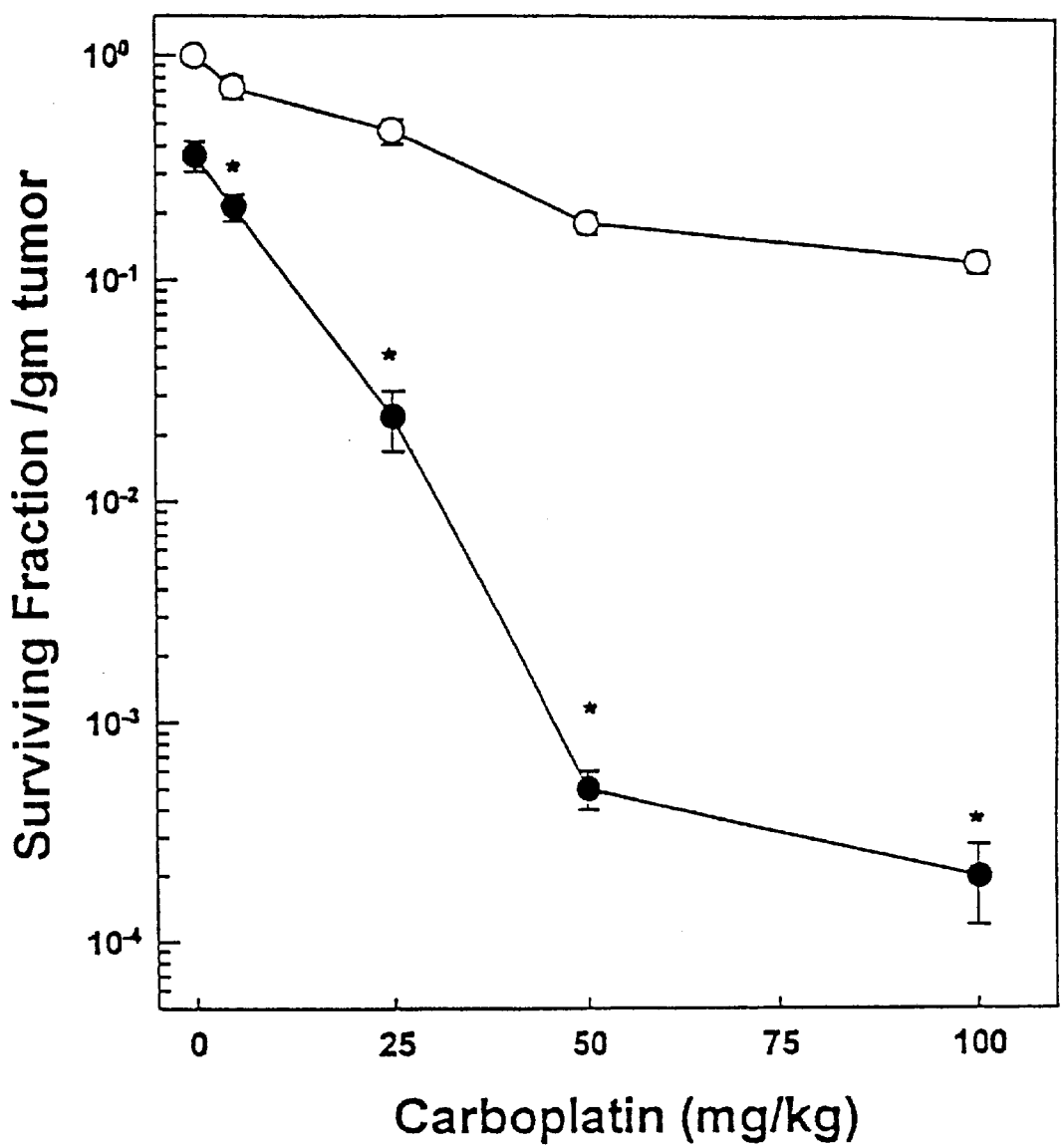
FIGS. 6a and 6b graphically represent the results of dose-dependent carboplatin-mediated cytotoxicity assays employing $1,25D_3$ pretreatment.

The excision clonogenic kill assay was employed wherein SCCVII/SF tumor bearing animals at 14 days post implantation were treated i.p. for 3 days with 0.5 mg/kg/day of $1,25D_3$. On the third day animals received varying doses of carboplatin. After 24 hours, tumors were harvested, dissociated, and plated for a 7 day incubation. As shown in FIG. 6a, pre-treatment for 3 days with $1,25D_3$ before carboplatin resulted in a significant enhancement of clonogenic cell kill when compared to animals treated with carboplatin or $1,25D_3$ alone. A significant increase in clonogenic tumor cell kill was observed at each carboplatin dose tested.

Figure 6B:
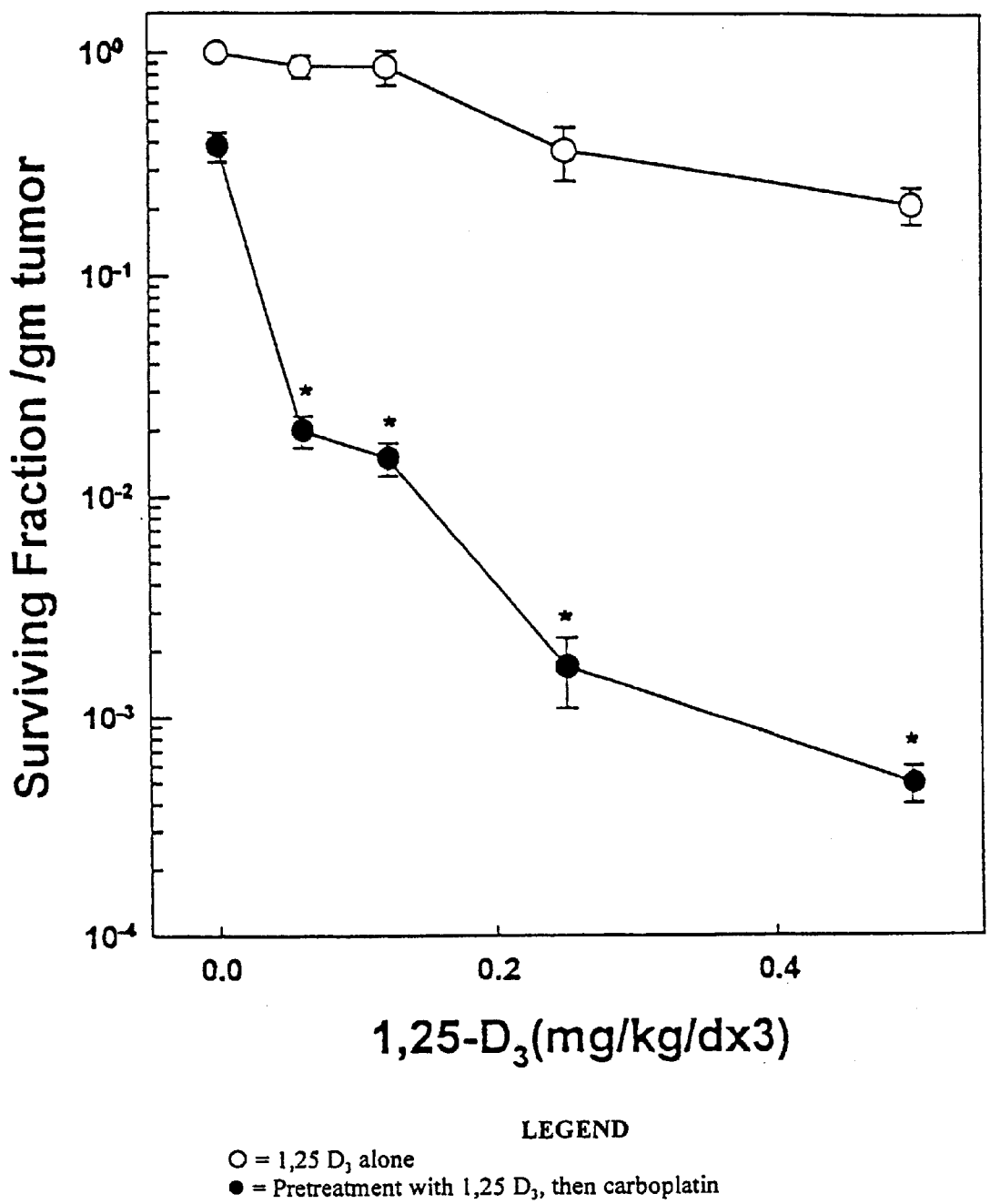

In a second experiment, the excision clonogenic kill assay was employed wherein the SCCVII/SF tumor bearing animals at 14 days post implantation were treated i.p. for 3 days with $1,25D_3$ at varying doses. On the third day animals received 50 mg/kg/day carboplatin. After 24 hours, tumors were harvested, dissociated, and plated for a 7 day incubation. As shown in FIG. 6b, pre-treatment with $1,25D_3$ before carboplatin resulted in a significant enhancement of clonogenic cell even at the lowest doses of $1,25D_3$. A significant increase in clonogenic tumor cell kill was observed at each carboplatin dose tested as compared to carboplatin alone. No animals became hypercalcemic at any of the $1,25D_3$ doses tested.

Example 7

This example demonstrates the potential for sensitizing tumor cells to the effects of conventional cytotoxic paclitaxel by pretreatment with a vitamin D analog.

Figure 7:
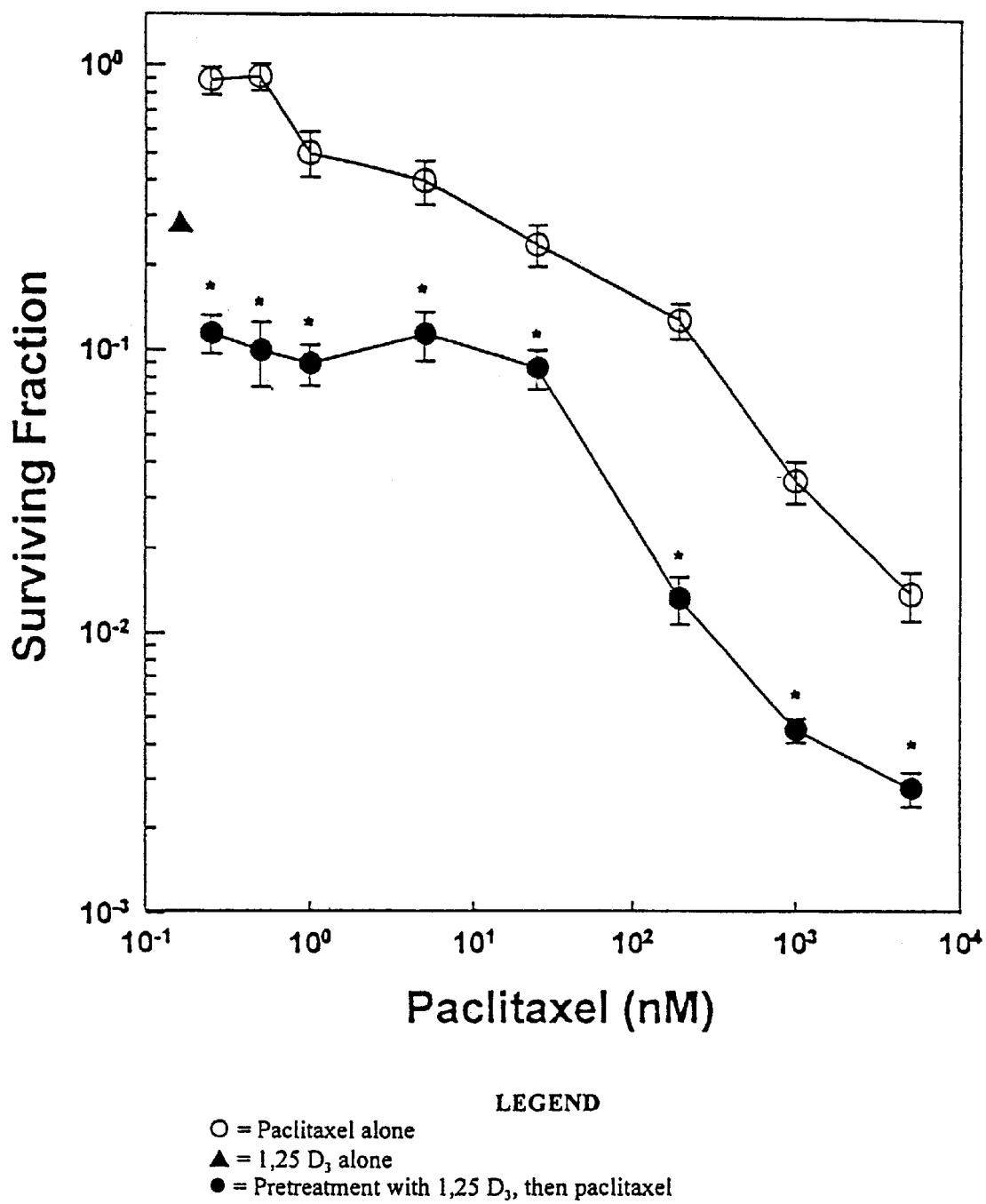
FIG. 7 is a graphic depiction of the effect of $1,25D_3$ pretreatment on paclitaxel-mediated tumor cytotoxicity. Each point represents the mean±SD (3 replicates). Values significantly different than paclitaxel alone are shown with an asterisk: $*p<0.001$ (ANOVA).

Paclitaxel and $1,25D_3$ were tested alone and in combination using the in vitro clonogenic assay as described above. As shown in FIG. 7, pre-treatment of cells with $1,25D_3$ significantly enhanced clonogenic cell kill when compared to $1,25D_3$. It was also observed that concurrent administration of $1,25D_3$ and paclitaxel did not result in an enhancement of clonogenic cell kill over paclitaxel alone.

Example 8

This example demonstrates the enhancement of paclitaxel-mediated in vivo anti-tumor activity by pretreatment with $1,25D_3$.

Figure 8:
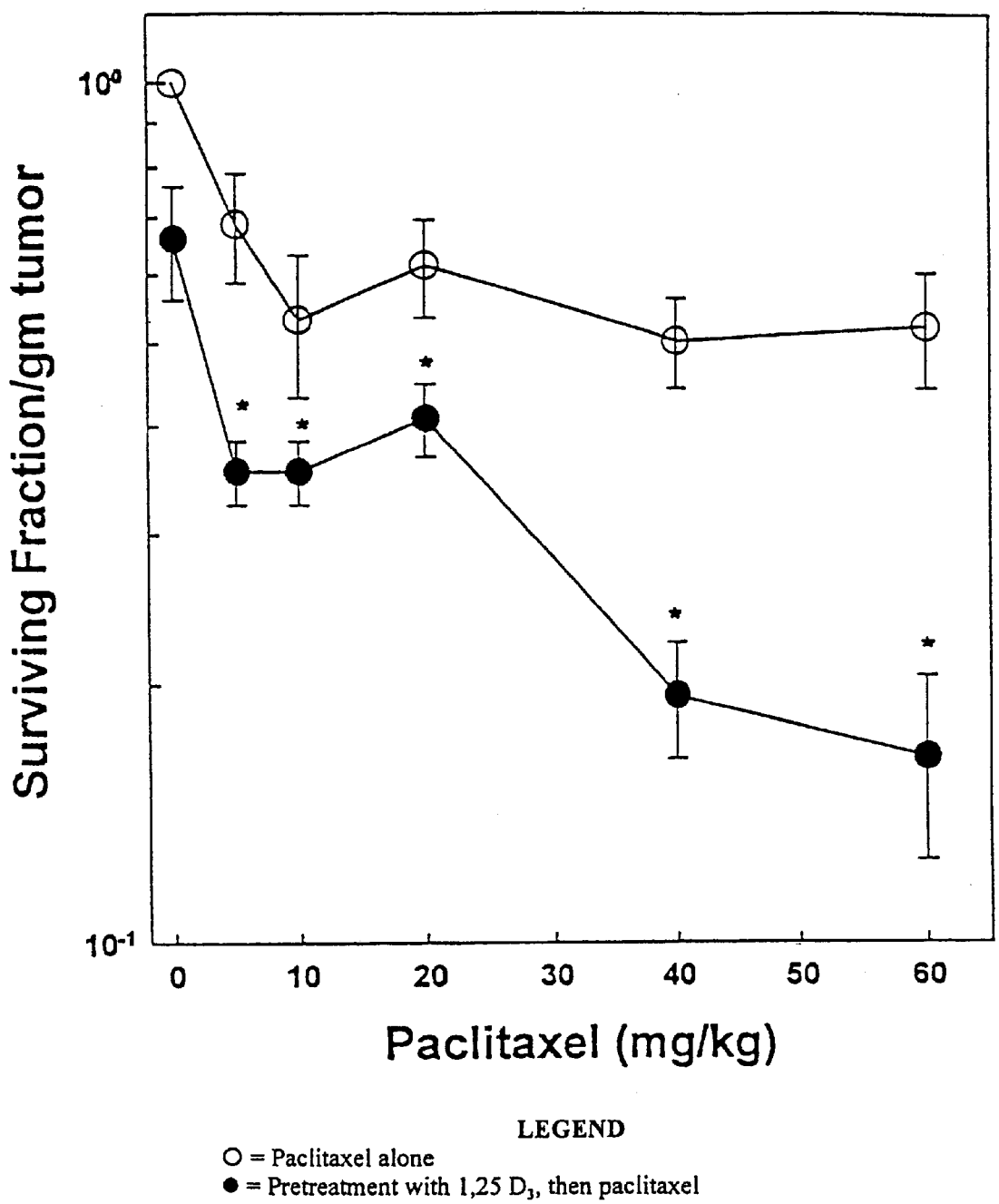
FIG. 8 is a graphic depiction of paclitaxel dose-dependent in vivo clonogenic tumor-cell cytotoxicity in combination with $1,25D_3$ pretreatment. Each point represents the mean±SD for total clonogenic cells/g tumor (3–5 mice/treatment group). Values significantly different than paclitaxel alone are shown with an asterisk: $*p<0.001$ (ANOVA).

The excision clonogenic kill assay was employed wherein SCCVII/SF tumor bearing animals at 11 days post implantation were treated i.p. for 3 days with 0.2 µg/day of $1,25D_3$. On the third day animals received varying doses of paclitaxel. After 24 hours, tumors were harvested, dissociated, and plated for a 7 day incubation. As shown in FIG. 8, pre-treatment for 3 days with $1,25D_3$ before paclitaxel resulted in a significant enhancement of clonogenic cell kill when compared to animals treated with paclitaxel alone. A significant increase in clonogenic tumor cell kill was observed at each paclitaxel dose tested as compared to paclitaxel alone. No animals became hypercalcemic during these treatments.

Example 9

This example demonstrates the enhancement of in vivo paclitaxel-mediated anti-tumor activity by pretreatment with $1,25D_3$.

Figure 9:
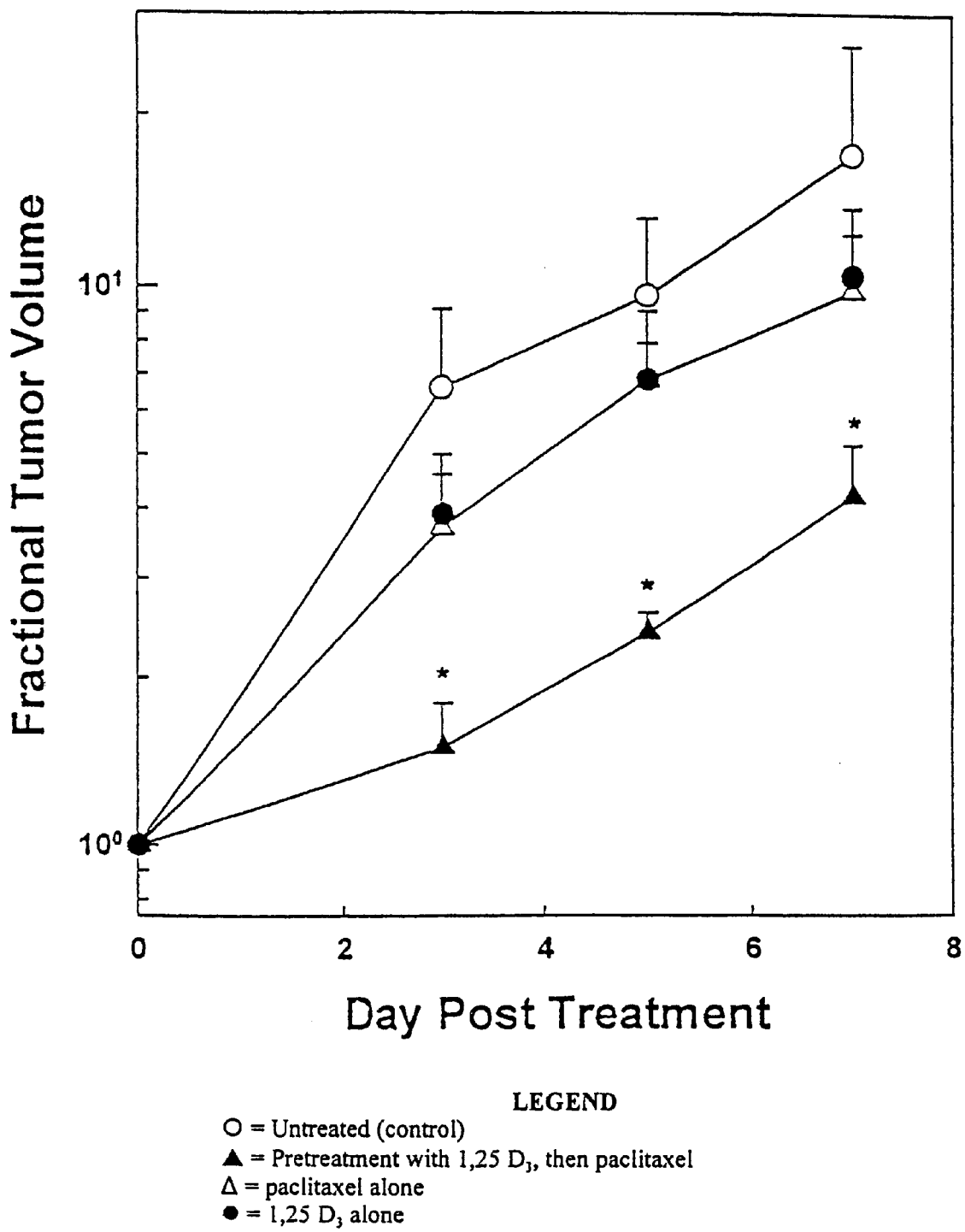
FIG. 9 is a graphic depiction of the enhancement of the in vivo effects of $1,25D_3$ by paclitaxel pretreatment. Each point represents the mean±SD for 8–10 animals. Values significantly different than paclitaxel alone are shown with an asterisk: $*p<0.001$ (ANOVA).

The tumor regrowth assay was employed wherein SCCVII/SF tumor-bearing mice (day 7 post implantation) were treated with 0.2 μg/mouse $1,25D_3$ administered continuously. At the end of $1,25D_3$ administration, paclitaxel was injected i.p. at 40 mg/kg. No treatment or single treatment animals were injected with vehicle (PBS) or implanted with sham pumps depending on the treatment group. As shown in FIG. 9, animals experienced a significant decrease in fractional tumor volume when pre-treated with $1,25D_3$ before paclitaxel as compared to treatment with either agent alone.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of killing a targeted cell in vivo comprising the steps of (a) first administering to a targeted cell in vivo a vitamin D derivative and (b) subsequently administering to said cell a cytotoxic agent, wherein said cytotoxic agent is paclitaxel or cyclophosphamide.

2. The method of claim 1, wherein said cell is a neoplastic cell.

3. The method of claim 1, wherein said cell is within a tumor.

4. The method of claim 1, wherein said vitamin D derivative is $1,25D_3$.

5. The method of claim 1, wherein said vitamin D derivative is an analog of $1,25D_3$.

6. The method of claim 5, wherein said analog is a nonhypercalcemic analog.

7. The method of claim 5, wherein said analog is Ro23-7553 or Ro24-5531.

8. The method of claim 1, wherein said cytotoxic agent is paclitaxel.

9. The method of claim 1, wherein said cytotoxic agent is cyclophosphamide.

10. A method of retarding the growth of a tumor in vivo comprising the steps of (a) first administering to tumor in vivo a vitamin D derivative and (b) subsequently administering to said tumor a cyeotoxic agent, wherein said cytotoxic agent is paclitaxel or cyclophosphamide.

11. The method of claim 10, wherein said vitamin D derivative is $1,25D_3$.

12. The method of claim 10, wherein said vitamin D derivative is an analog of $1,25D_3$.

13. The method of claim 12, wherein said analog is a nonhypercalcemic analog.

14. The method of claim 12, wherein said analog is Ro23-7553 or Ro24-5531.

15. The method of claim 10, wherein said cytotoxic agent is paclitaxel.

16. The method of claim 10, wherein said cytotoxic agent is cyclophosphamide.

17. A method of killing a targeted cell comprising the steps of (a) first administering to a targeted cell a vitamin D derivative and (b) subsequently administering to said cell a cytotoxic agent, wherein said cytotoxic agent is paclitaxel or cyclophosphamide.

18. The method of claim 17, wherein said cell is a neoplastic cell.

19. The method of claim 17, wherein said cell is within a tumor.

20. The method of claim 17, wherein said vitamin D derivative is 1,25D3.

21. The method of claim 17, wherein said vitamin D derivative is an analog of 1,25D3.

22. The method of claim 21, wherein said analog is a nonhypercalcemic analog.

23. The method of claim 21, wherein said analog is Ro23-7553 or Ro24-5531.

24. The method of claim 17, wherein said cytotomic agent is paclitaxel.

25. The method of claim 17, wherein said cell is in vitro.

26. The method of claim 17, wherein said cytotoxic agent is cyclophosphamide.

27. A method of retarding the growth of a tumor comprising the steps of (a) first administering to a tumor a vitamin D derivative and (b) subsequently administering to said tumor a cytotoxic agent, wherein said cytotoxic agent is paclitaxel or cyclosphosphamide.

28. The method of claim 27, wherein said vitamin D derivative is 1,25D3.

29. The method of claim 27, wherein said vitamin D derivative is an analog of 1,25D3.

30. The method of claim 29, wherein said analog is a nonhypercalcemic analog.

31. The method of claim 29, wherein said analog is Ro23-7553 or Ro24-5531.

32. The method of claim 27, wherein said cytotoxic agent is paclitaxel.

33. The method of claim 27, wherein said tumor is in vitro.

34. The method of claim 27, wherein said cytotoxic agent is cyclophosphamide.

* * * * *